United States Patent [19]

Doi

[11] Patent Number: 4,676,242

[45] Date of Patent: Jun. 30, 1987

[54] LASER KNIFE

[75] Inventor: Yuzuru Doi, Tokyo, Japan

[73] Assignee: Asahi Kogaku Kogyo Kabushiki Kaisha, Tokyo, Japan

[21] Appl. No.: 828,174

[22] Filed: Feb. 11, 1986

[30] Foreign Application Priority Data

Feb. 12, 1985 [JP] Japan .................. 60-24870

[51] Int. Cl.$^4$ .................. A61B 17/32; A61B 17/36
[52] U.S. Cl. .................. 128/303.1; 128/398; 137/13; 137/15; 137/156
[58] Field of Search .......... 128/303.1, 362, 395–398; 604/30, 31, 34, 50, 51, 118, 119

[56] References Cited

U.S. PATENT DOCUMENTS

| | | | |
|---|---|---|---|
| 3,065,749 | 11/1962 | Brass | 604/119 |
| 3,407,748 | 10/1968 | Mamo | 604/52 |
| 3,858,577 | 1/1975 | Bass et al. | 128/398 |
| 4,122,853 | 10/1978 | Smith | 128/303.1 |
| 4,185,633 | 1/1980 | Prozorov et al. | 128/303.1 |
| 4,299,221 | 11/1981 | Phillips et al. | 604/30 |
| 4,313,431 | 2/1982 | Frank | 128/303.1 |

Primary Examiner—Lee S. Cohen
Assistant Examiner—David Shay
Attorney, Agent, or Firm—Finnegan, Henderson, Farabow, Garrett and Dunner

[57] ABSTRACT

A laser knife which supplies water to a rod member applying laser radiation to tissue or the like by means of using the air supply passing air between a fiber optic laser transmitting member and a hollow tube. Air issuing from the tube may be bled to the atmosphere through a bleed valve. Closure of the bleed valve pressurizes an annular space in flow communication with the upper portion of a fluid supply tank. Pressurization of the tank forces fluid from the tank into an annular space within the device through orifices in flow communication with grooves adjacent the rod member. In such a manner, the pressurization of the air supply system causes fluid to flow over the rod member to prevent adherence of tissue and the like to the end of the rod transmitting the laser radiation.

6 Claims, 2 Drawing Figures

LASER KNIFE

BACKGROUND OF THE INVENTION

The present invention relates to a medical laser knife having a rod member adapted to emit, a laser beam while in contact with tissue making it possible to coagulate body fluids or cut the tissue. More particularly, the invention relates to means for supplying water to the end of the rod member to prevent adhesion of burnt materials thereto.

Conventionally, there are practiced surgical treatments where a laser beam is transmitted through fiber optics to a transparent rod member and the rod member is brought into contact with tissue to either coagulate the body fluids associated therewith or to cut the tissue. In such surgical treatments, the laser beam is applied directly to the tissue and the rod member may be held directly on the tissue whereupon coagulated body fluids or the diseased tissue may stick to the rod member. Inasmuch as this material must be removed for effective operation of the device there are provided conventional means of applying a jet of distilled water to the rod member during its use.

Generally, laser knives are provided with a gas supply system for passing a gas stream over the end of the fiber conducting the laser beam. In order to provide a separate water supply system to apply water to the end of the rod member, it has been necessary to modify a part of the gas supply system and to provide a separate water supplying system that includes a pump. Such a separate water supply system with its attendant pump is a disadvantage in such devices because it is an entirely separate subsystem that must be manufactured and supplied with the device. It has been the practice to pass water within the clearance between the fiber optics transmitting the laser beam and a hollow tube surrounding the fiber optics. Such a configuration has, however, serious drawbacks in that when water is passed through the space between the fiber optics and a surrounding hollow pipe, water drops remain within that space after use of the device. This is undesirable where gas or air is also to be jetted and adversely affects the sterilization of the laser knife, both of which are serious drawbacks to conventional devices.

It is an object of this invention to eliminate the above-described shortcomings of conventional laser knives. More specifically, it is an object of the invention to provide a laser knife which, in order to supply water to the end of the rod member transmitting laser beam instead of a separate water supply system, the air supplying mechanism provided for an ordinary laser knife is utilized.

SUMMARY OF THE INVENTION

In order to accomplish these and other objects of the invention, there is provided a laser knife which includes a fiber optic means for transmitting a laser beam. A hollow tube surrounds the fiber optic means and is separated therefrom to form a space therebetween. A rod member is optically coupled to the fiber optic means and is disposed to emit the laser beam from the end thereof. A fluid supply means is provided along with means for flowing fluid along the rod member toward the end emitting the laser beam. The fluid flow means is in flow communication with the fluid supply means. Gas supply means are in flow communication with the space between the hollow tube and the fiber optic means and the gas supply means applies pressurized gas within that space. Conduit means in flow communication with this space and the fluid supply means apply gas pressure to the fluid to induce flow of the fluid upon application of the gas pressure.

Preferably, the laser knife includes valve means in flow communication with the space between the hollow tube and the fiber optic means where closure of the valve applies gas pressure to the fluid supply.

BRIEF DESCRIPTION OF THE INVENTION

DESCRIPTION OF THE PREFERRED EMBODIMENT

An embodiment of this invention will be described by reference to the accompanying drawings.

Figure 1:
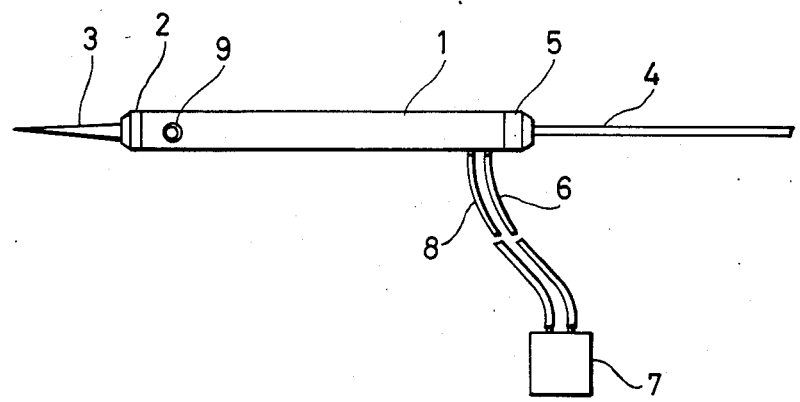
FIG. 1 is an overall external view showing an embodiment of the invention.
Figure 2:
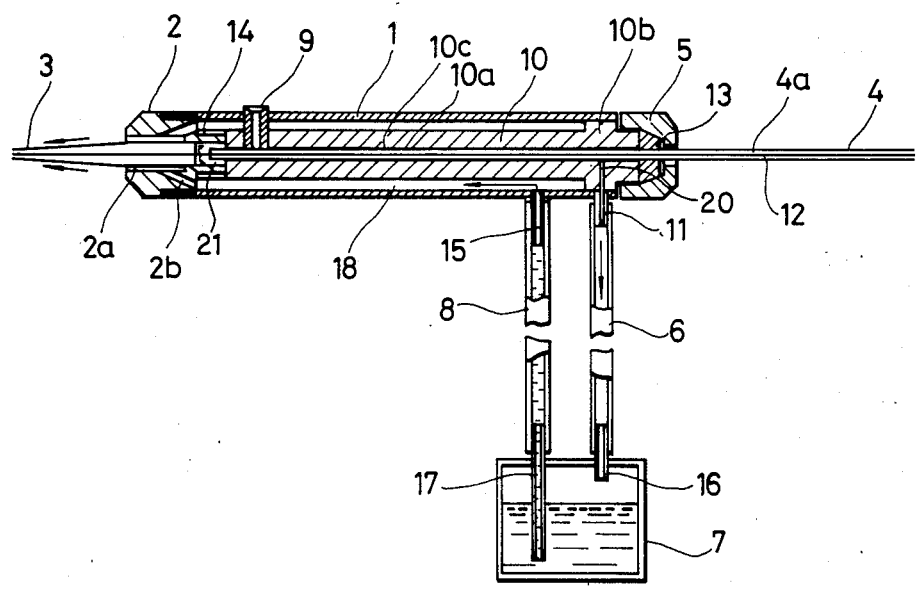
FIG. 2 is a cross-sectional view showing the internal structure of the embodiment of FIG. 1.

FIG. 1 shows the external appearance of one embodiment of this invention. A conical rod member 3 is secured through a front end cap 2 to one end of a cylindrical outer body 1. A hollow tube 4 projects through a rear end cap 5 which is affixed to the cylindrical body 1. The hollow pipe 4 contains and protects a fiber optic member 12 that is inserted within the hollow tube 4 in such a manner that there is an annular clearance between the fiber optic member 12 and the interior surface of the hollow tube 4. This annular clearance or space 4a is used to supply air to the device. In this embodiment, air is supplied from a conventional air supply means (not shown) through the annular space depicted in FIG. 2 as 4a. The air applied through the hollow tube 4 to the annular space 4a jets from one end of the hollow tube 4. The hollow tube 4 is located within a hole 10a in the support member 10 and is spaced within the hole 10a to form an annular gap 10c. An air bleed valve 9 is in flow communication with the annular gap 10c (and the previously noted space 4a) in such a position that the operator of the laser knife can position a thumb over the bleed valve when gripping the cylindrical body 1. Also in flow communication with the annular space 10c is an orifice in flow communication with an air supply nipple 11. The air supply nipple 11 is connected to an air supply conduit 6 in flow communication with the fluid supply tank 7. In such a manner, air pressure applied to the interior of the hollow tube 4 if not bleed from the annular space 10c by the bleed valve 9 is applied through the orifice into the air supply nipple 11 through the air supply conduit 6 to the upper portion of the fluid supply tank 7. As will be described in more detail with respect to FIG. 2, the application of air pressure to the fluid supply tank 7 causes the flow of fluid ultimately to the end of the rod member 3.

A generally cylindrical support member 10 is arranged within the cylindrical body 1. The support member 10 in the present embodiment includes a threaded portion 10b which is larger in diameter than the body of the remainder of the support member and engages internal threads within the cylindrical body 1. The support member 10 has a central opening 10a formed along the central axis disposed to receive the hollow tube 4. The end of the hollow tube 4 protrudes into the space 21 formed on one end of the support member 10 adjacent the rod member 3. The front end of the fiber optic member protrudes into the space 21 adjacent the rod member 3 and is separated from 1 to 3 mm from the end face of the rod member 3. The rod member 3 is secured to the hole in cylinder 1 by means of the front end cap 2 which is threadably engaged within the cylindrical body 1.

The aforementioned rear end cap 5 compresses a circular truncated cone-shaped rear seal 13 on a protrusion of the support member 10. By means of the rear end cap 5 and the elastic seal 13 the hollow tube 4 is affixed within the device such that there is a predetermined clearance (the annular gap 10c) between the hollow pipe 4 and the interior surface of the opening 10a. The support member 10 includes at one end an opening disposed to receive an annular protrusion formed on the end face of the front end cap 2. Leakage of air from the interior of the device is prevented by a front seal 14. The construction of the opening on the front end of the member 10 disposed to receive the annular protrusion from the front end cap 2 serves to align the axis of the rod member with the optical axis of the fiber optic member 12 at that portion of the device. Front cap end 2 further includes several grooves (two in this embodiment) 2a having a predetermined length that extend along the side surface of the rod member 3. The grooves are in flow communication with orifices 2b which are formed obliquely in the front end of cap 2. The orifices 2b are in flow communication with an annular fluid space 18 formed between the cylindrical body 1 and the support member 10. The annular fluid space 18 is in flow communication with a water supply nipple 15 which is fixedly secured to the cylindrical body 1. The fluid supply conduit 8 connects the fluid supply nipple 15 with the fluid outlet conduit 17 which is disposed within the fluid supply tank 7 such that its inlet adjacent the bottom of the tank.

The fluid supply tank 7 is closed except for the air supply conduit 16 and the fluid supply outlet conduit 17. The lower end of the air supply conduit is positioned above the level of the fluid in tank 7.

The laser knife of the present invention constructed as described above operates in the following manner. Air supply means (not shown) supply air through the annular space 4a between the fiber optic member 12 and the hollow tube 4. The air thus supplied jets from the end of the hollow tube 4 into the space 21 formed at the end of the support member 10. Because air leakage is prevented by the front seal 14 and the rear seal 13, the air thus jetted is supplied through the annular gap 10c between the hollow tube 4 and the interior opening 10a through the member 10 to the air bleed valve 9 and the nipple 11. If the air bleed valve 9 is closed, the air is forced from the nipple 11 through the air supply conduit 6 into the fluid supply tank 7. The air within the tank applies pressure to the liquid fluid in the tank 7 and the fluid is caused to flow through the fluid supply outlet conduit 17, the fluid supply conduit 8 into the annular fluid space 18 between the cylindrical body 1 and the support member 10. The fluid then passes through orifices 2b into the grooves 2a and on to the rod member 3 to issue from the end of the rod member.

When the bleed valve 9 is open, as for example by a removal of the thumb from the opening in the bleed valve, the air jetting from the end of the hollow pipe tube 4 flows through the bleed valve and no air pressure is applied to the fluid supply tank 7. This causes the flow of water from the rod member 3 to stop.

As is apparent from the above description, the present invention supplies liquid to the rod member by supplying pressure from the air supply means rather than a totally separate fluid pumping mechanism. In such a manner, water or fluid can be applied to the rod member to prevent the adhesion of coagulated body fluids or tissue. Furthermore, the flow of water to the rod member can be readily controlled using the thumb of the hand that grips the device. Furthermore, the laser knife, according to the present invention, can be readily sterilized and manufactured at low cost.

The present invention has been disclosed in terms of a preferred embodiment, but the invention is not limited thereto. The scope of the invention is defined by the appended claims and their equivalents.

What is claimed is:

1. A laser knife comprising:
   fiber optic means for transmitting a laser beam;
   a hollow tube surrounding said fiber optic means being separated therefrom to form a space therebetween;
   a rod member optically coupled at a first end to said fiber optic means and disposed to emit said laser beam from a second end;
   fluid supply means;
   means for flowing said fluid along said rod member toward said second end emitting said laser beam, said fluid flow means being in flow communication with said fluid supply means; and
   gas supply means in flow communication with said space disposed to apply pressurized gas to said space, conduit means in flow communication between said space and said fluid supply means for applying gas pressure to said fluid to induce flow of said fluid upon application of said gas pressure.

2. The laser knife of claim 1 including valve means in flow communication with said space whereupon closure of said valve means applies gas pressure to said fluid supply.

3. The laser knife of claim 2 wherein said valve means comprises a conduit in flow communication with said space whereupon manual closure of said conduit applies gas pressure to said fluid.

4. The laser knife of claim 2 wherein said knife includes a generally cylindrical support member having a hole passing along its central axis, said hole having an inside diameter greater than the outside diameter of said hollow tube, said hollow tube being disposed within said hole to form an annular gap between said tube and said inside diameter, said annular gap being in flow communication with said space.

5. The laser knife of claim 4 wherein said valve means comprise a closable orifice in flow communication with said annular gap.

6. The laser knife of claim 4 wherein said support member includes an orifice leading from said annular gap, said knife including gas conduit means leading from said orifice to said fluid supply means.

* * * * *